United States Patent [19]
Bressler et al.

[11] Patent Number: 5,146,637
[45] Date of Patent: Sep. 15, 1992

[54] FEMALE URINE COLLECTION APPARATUS

[76] Inventors: Mark Bressler, 3566 Liberty La., Marietta, Ga. 30062; Stephen Blank, 5290 Woodridge Forest Trail, Atlanta, Ga. 30327

[21] Appl. No.: 645,209

[22] Filed: Jan. 24, 1991

[51] Int. Cl.$^5$ ............................................. A47K 11/00
[52] U.S. Cl. ..................................... 4/445; 4/144.1; 141/372
[58] Field of Search ................... 4/144.1, 144.2, 315, 4/445, 463; 141/372

[56] References Cited

U.S. PATENT DOCUMENTS

| | | | |
|---|---|---|---|
| D. 267,342 | 12/1982 | Laible | D24/57 |
| 1,405,197 | 1/1922 | Franke | 141/372 |
| 1,455,255 | 5/1923 | Kapelman | 4/483 |
| 1,733,080 | 10/1929 | Hamilton | 4/242 |
| 2,146,206 | 2/1939 | Elliott | 4/483 |
| 2,560,199 | 7/1951 | Trichel et al. | 4/144.1 |
| 2,603,795 | 9/1952 | Terlizzi | 4/479 |
| 2,801,424 | 8/1957 | Mercer | 4/144.1 X |
| 3,131,403 | 5/1964 | Hill | 4/144.3 |
| 3,250,303 | 5/1966 | Sollmann | 141/372 |
| 3,383,713 | 5/1968 | Adams | 4/144.1 |
| 3,588,921 | 6/1971 | Nagel | 4/315 X |
| 3,625,654 | 12/1971 | Van Duyne | 4/144.2 |
| 3,654,638 | 4/1972 | Nye | 4/144.1 |
| 4,203,169 | 5/1980 | Dale | 4/144.1 |
| 4,422,188 | 12/1983 | Strutton et al. | 4/144.1 |
| 4,531,245 | 7/1985 | Lowd et al. | 4/144.1 |
| 4,559,649 | 12/1985 | Burnett | 4/144.1 |
| 4,815,151 | 3/1989 | Ball | 4/144.3 |

FOREIGN PATENT DOCUMENTS

| | | | |
|---|---|---|---|
| 2456507 | 1/1981 | France | 4/144.1 |
| 421433 | 3/1967 | Switzerland | 4/445 |

OTHER PUBLICATIONS

Scandinavian Journal of Clinical & Laboratory Investigations, 1962, B. Isaksson-Device for the Separate Collection of Human Urine & Feces, p. 418.

Primary Examiner—Henry J. Recla
Assistant Examiner—Robert M. Fetsuga
Attorney, Agent, or Firm—Dykema Gossett

[57] ABSTRACT

A hands-free female and male urine collection apparatus has a body with connected side, front, rear and bottom wall, with the side and front walls inclined inwardly. Portions of the bottom wall are inclined downwardly from the front wall towards the back wall and opposed portions of the bottom wall are inclined downwardly and inwardly from the side walls. The bottom wall terminates in a funnel shaped drain having a depending outlet. An adapter depends from the bottom wall and includes a flange to slidably receive a flanged cup. A plurality of right angularly related mount strips or other mount device extends radially outward from the body and are adapted to supportably bear upon a toilet bowl.

5 Claims, 1 Drawing Sheet

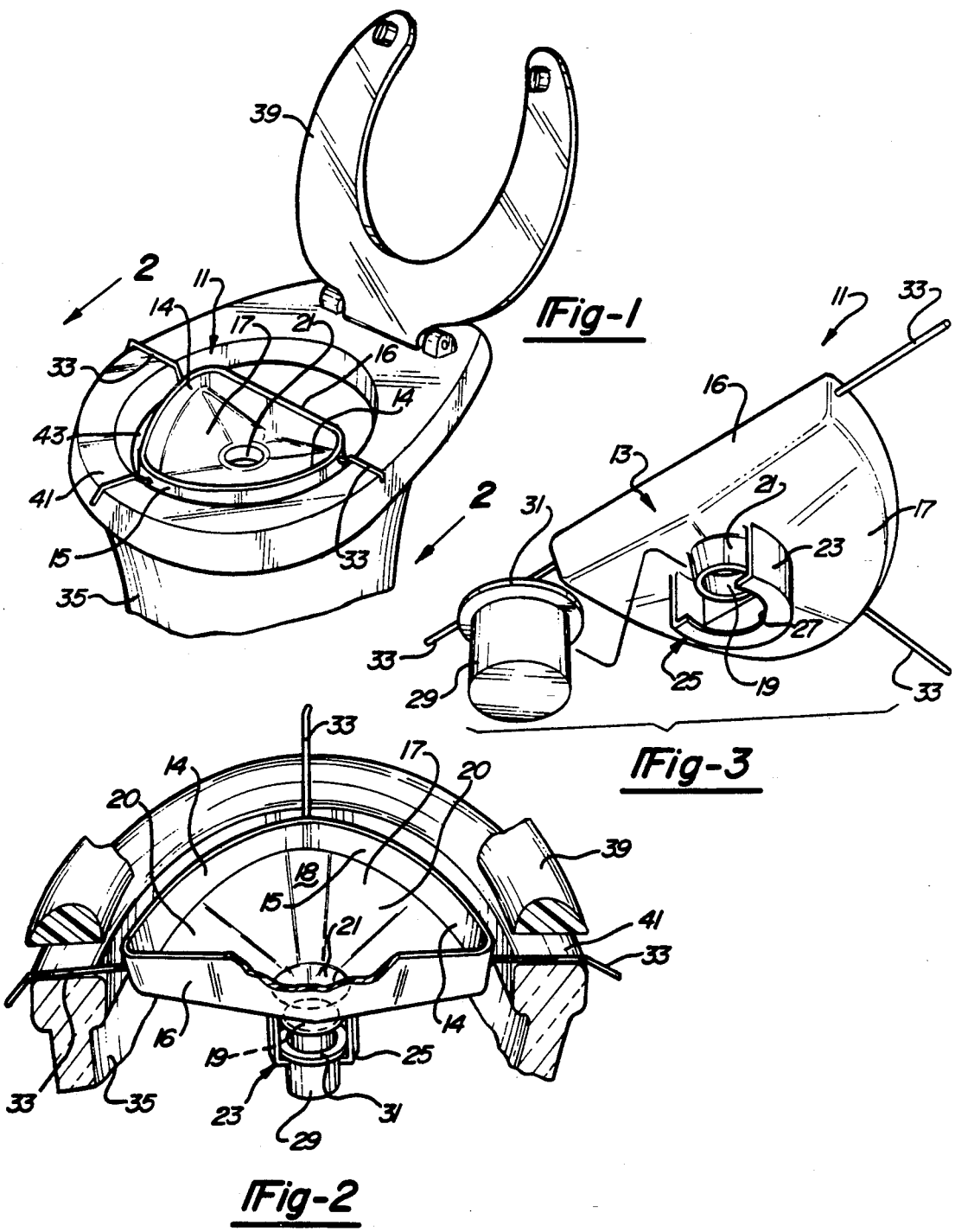

FEMALE URINE COLLECTION APPARATUS

FIELD OF INVENTION

The present invention relates to female urine collection apparatus, and more particularly to hands-free collection apparatus supportably mounted upon a toilet bowl.

BACKGROUND OF THE INVENTION

Previously many efforts have been made in providing for female urine specimens many of which have been unsatisfactory, including vessels and cups due to the difficulty of holding, filling, transport and storage in a sanitary manner.

Various efforts have been made to provide a device either hand-held or otherwise supported upon a toilet bowl in order to minimize the personal effort involved in providing a urine specimen.

Difficulties have been encountered in properly mounting the apparatus so that it is self-supporting upon a toilet bowl and for the collection of a urine specimen therein and for its transport or storage of the specimen therein or for transfer to a second container.

PRIOR ART

Various patent efforts have been made to disclose devices particularly useful in the collection of urine specimens and in many cases female urine collection apparatus, though not limited thereto. The following patents are illustrative of prior art efforts:

| Patent No. | Inventor | Title |
| --- | --- | --- |
| D 267,342 | Laible | Design for Specimen Collection |
| 3,131,403 | Hill | Adult Urine Specimen Collector |
| 3,625,654 | Van Duyne | Urine Collection Device |
| 4,203,169 | Dale | Urine Collection Device |
| 4,422,188 | Strutton, et al. | Micturition Adaptor for Conversion of a Male Bed Urinal to Female Use |
| 4,531,245 | Lowd, et al. | Personal Urinal Device |
| 4,559,649 | Turnett | Urine Specimen Collection System |
| 4,815,151 | Ball | Urinary Guide Apparatus and Method of Using the Same |

Publication:
Scandinavian Journal of Clinical and Laboratory Investigations, 1962, B. Isson, Device for the Separate Collection of Human Urine and Feces, Page 4–18.

SUMMARY OF THE INVENTION

An important feature of the present invention is to provide an improved hands-free easy to use female urine collection apparatus which is mountable upon a toilet bowl for convenient use.

An important feature is to provide open top body with connected side, front, rear and bottom walls with the respective side and front walls inclined downwardly and inwardly and with the bottom wall suitably inclined towards central portions thereof and towards the rear wall terminating in a funnel shaped drain spaced from the rear wall and having a depending outlet.

As another feature an adapter extends from and is connected to the bottom wall of the apparatus body underlying the outlet. The adapter includes a pair of opposed L-shaped mount flanges adapted to supportably receive the top flange of a flanged cup which is slidably and removably positioned upon the mount flanges in registery with the outlet for collecting liquids.

Still another feature is to provide upon the apparatus body a plurality of right angularly related mount strips at their one ends connected to said body and extending radially outward thereof adapted for supportive positioning over a toilet bowl.

As another feature the back wall of the body is straight and interconnects the adjacent ends of the side walls thereof.

As still another feature the side walls are curved inwardly and merge with the front wall and wherein the side and front walls are arranged substantially in the shape of a parabola.

As still another feature, the present apparatus is constructed of a material of a throw away nature and discardable such as paper or plastic or of a sterilizable material such as Vitreous China and stainless steel.

As still another feature, the invention is directed to the combination with a toilet bowl having a generally continuous top flange and a toilet seat, of the present female urine collection apparatus and wherein a plurality of mount strips connected to the body are so arranged as to supportably overlie the top flange of the toilet bowl so that the apparatus extends across the front half of the toilet bowl opening.

As still another feature, the adapter which underlies the apparatus and the outlet for the funnel-shaped drain includes a back wall portion limiting assembly of the flanged cup thereon so as to centrally position the cup with respect to said outlet.

These and other objects and features will be seen from the following specification and claims in conjunction with the appended drawing:

THE DRAWING

FIG. 1 is a front perspective view of the present female urine collection apparatus as positioned over a toilet bowl fragmentarily shown, and including a seat.

FIG. 2 is a fragmentary sectional view taken on line 2-2 of FIG. 1, and with the seat in a down position and fragmentarily shown.

FIG. 3 is a bottom perspective view of the present female urine collection apparatus.

It will be understood that the above drawing illustrates merely a preferred embodiment of the invention, and that other embodiments are contemplated within the scope of the claims hereinafter set forth.

DETAILED DESCRIPTION OF THE PREFERRED EMBODIMENT OF THE INVENTION

Referring to the drawing, the present female urine collection apparatus is generally indicated at 11 and includes an open top collector body 13 in the general shape in plan of a parabola.

Said body includes a pair of generally curved opposed side walls 14 which merge in the arcuate front wall 15. The respective side and front walls are inclined inwardly and downwardly, FIG. 1, and terminate in the bottom wall 17.

The back wall 16 is straight and extends across the rear ends of the respective opposed side walls 14.

The respective side walls and front wall are inclined downwardly and inwardly and merge with bottom wall 17. Front portions 18 of the bottom wall are inclined downwardly and inwardly from the front wall 15 and extend toward back wall 16. Opposed side portions 20 of bottom wall 17 are inclined downwardly and inwardly from side walls 14.

The bottom wall 17 is generally inclined downwardly and inwardly and toward back wall 16. The respective portions 18 and 20 of the bottom wall terminate in a funnel shaped drain 21 arranged adjacent to and centrally of and spaced from back wall 16. Said drain includes an outlet opening 19.

Adapter 23 or cup holder of semicircular shape underlies and partly surrounds the funnel shaped drain 21 centrally of outlet 19 and is secured to said bottom wall. The adapter includes a semicircular mount flange 25 adapted to supportably receive the top flange 31 of cup 29.

Adapter 23 includes a stop portion 27, FIG. 3, to limit forward assembly of cup 29 and its flange 31 onto mount flange 25 so that the cup is centrally positioned relative to outlet 19 of drain 21.

In order to support the apparatus body 13 upon toilet bowl 35, having a conventional seat 39 and a top flange 41, there are provided upon body 13 a plurality of right angularly related radially extending mount strips 33. Said strips at their one ends are connected to the body and extend radially outward therefrom. The said strips 33, sometimes referred to as support bars or support ears, provide a suspension and mounting for the body 13 holding it in a horizontal position upon the toilet bowl flange 41 normally occupying the front one half of the toilet opening 43, centrally thereof. The ears or tabs 33 may be preshaped and protrude outwardly from each corner of said body.

In normal use the seat 39 is hinged to the horizontal position shown in FIG. 2 for the convenience of the user. The seat overlies the respective support bars or strips 33 for retaining them against accidental displacement and for maintaining the body 13 centrally of the toilet bowl and its opening 43.

Thus, the present female urine collection apparatus is adapted for hands-free operation and with its open top supportably positioned upon the front half of the toilet bowl 35, FIG. 1, for use in the collection of a urine specimen within the removably positioned cup 29.

The present adapter 23 with its stop wall portion 27 assures that the cup will centrally underlie the funnel shaped drain 21 and its opening 19 for accurately collecting any fluids which accumulate in the body 13 of the apparatus. Adaptor 23 forms 180° of a circle with allowance for overflow of excess urine.

Thereafter, the cup may be easily removed from the adapter and suitably covered with a conventional air tight cover for whatever investigative use is required by the physician.

In order to conform the present apparatus to a particular toilet bowl flange dimensions, the respective support bars or strips 33 are flexible to some extent to facilitate proper assembly and central positioning of the apparatus with respect to the toilet bowl opening 43 as best shown in FIGS. 1 and 2.

The arrangement of the adapter 23 and its inturned mount flanges 25 provided a convenient means for accurately mounting the cup 29 and its flange 31 so as to underlie the funnel-shaped drain 21 and its outlet 19 for the accurate delivery of a urine specimen into the cup.

Having described our invention, reference should now be had to the following claims.

We claim:

1. A female urine collection apparatus comprising an open top body having connected side, front, rear and bottom walls;

the side and front walls being connected and inclined downwardly and inwardly towards said bottom wall:

portions of said bottom wall being inclined downwardly and rearwardly from said front wall toward said rear wall;

opposed portion of said bottom wall being inclined downwardly and inwardly from said side walls;

said bottom wall portions terminating in a funnel-shaped drain spaced from said rear wall and having a depending outlet;

an adapter depending from and connected to said bottom wall underlying said outlet;

a semicircular mount flange on said adapter and spaced from said drain;

a cup having a top flange slidably and removably positioned upon said mount flange in registry with said outlet for collecting liquids; and a plurality of right angularly related mount strips at their one ends connected to said body and extending radially outward thereof adapted for supportive positioning over a toilet bowl.

2. In the collection apparatus of claim 1, further comprising said back wall being straight and interconnecting the adjacent ends of said side walls, said side walls being curved inwardly and merging with said front wall.

3. In the collection apparatus of claim 1, said side and front walls being substantially in the shape of a parabola;

said back wall being straight and spanning the ends of said side walls.

4. In the collection apparatus of claim 1, further comprising said mount flange having a stop portion engagable with said cup for centrally positioning said cup under said outlet.

5. In combination with a toilet bowl having a generally continuous top flange and a toilet seat;

a female urine collection apparatus comprising an open top body having connected side, front, rear and bottom walls;

the side and front walls being connected and inclined downwardly and inwardly towards said bottom wall;

portions of said bottom wall being inclined downwardly and rearwardly from said front wall toward said rear wall;

opposed portions of said bottom wall being inclined downwardly and inwardly from said side walls;

said bottom wall portions terminating in a funnel-shaped drain spaced from said rear wall and having a depending outlet;

an adapter depending from and connected to said bottom wall underlying said outlet;

a semicircular mount flange on said adapter and spaced from said drain;

a cup having a top flange slidably and removably positioned upon said mount flange in registry with said outlet for collecting liquids;

a plurality of right angularly related mount strips at their one ends connected to said body and extending radially outward thereof adapted for supportive positioning over said top flange; and the toilet seat overlying said mount strips.

* * * * *